United States Patent [19]

Ludick

[11] Patent Number: Plant 5,681

[45] Date of Patent: Mar. 4, 1986

[54] HIBISCUS PLANT

[76] Inventor: Joseph E. Ludick, 13095 NE. 2nd Ave., North Miami, Fla. 33161

[21] Appl. No.: 578,478

[22] Filed: Feb. 9, 1984

[51] Int. Cl.[4] ..... A01H 5/00

[52] U.S. Cl. ..... Plt./54

[58] Field of Search ..... Plt./54

*Primary Examiner*—Robert E. Bagwill

[57] ABSTRACT

A novel hibiscus plant having double, tri-colored blooms and glossy foliage with good substance, borne on upright, vigorous branches.

2 Drawing Figures

1

A new, distinct variety of hibiscus plant, of the Rosa-sinensis species.

The plant is characterized as to novelty by its vigorous, upright habit of growth, its crisp green foliage, and its brilliant, long-lasting flowers.

A plant and flower of the new variety are shown in full color in the accompanying illustration.

A detailed description of the new variety follows, and to facilitate identification of the important colors, the color terminology adopted by The British Horticultural Colour Charts has been followed. (Reference is to "Horticultural Colour Charts" issued by The British Colour Council in two volumes, in collaboration with The Royal Horticultural Society, copyright by Robert F. Wilson, published 1938–1941.)

Hybridizer: J. E. Ludick, 13095 NE. 2nd Ave., North Miami, FL U.S. Citizen.

Plant characteristics:

*Parentage.*—Seedling resulting from definite breeding efforts. Parents — Lemon Chiffon and Munro Star.

*Growth.*—The plant is a vigorous upright growth, well-clothed with foliage. The ultimate height of the plant is 4 to 6 feet, with a spread of 3 feet.

*Branches.*—New branch growth is a light green (Scheeles Green 860) changing to a light brown as it matures. Bark is slightly rough.

*Growth habits.*—Branching starts just above the ground level and generally ascends.

*Foliage.*—The leaves are of good substance and are glossy. Shape. — The leaves are best described

2 as being broadly cordate, with the margin crenate. The apex of the leaf is acute, the base truncate. Color. — The upper surface of the leaf is 139 A Green. The underside is 137 B Green. Size. — Leaves are from $3\frac{1}{4}$ to $4\frac{1}{4}$ inches wide, and from $3\frac{1}{2}$ to $4\frac{1}{2}$ inches long. Petiole is 1 inch long. Arrangement. — Leaves are alternate on the stems. Veins. — Slightly lighter than leaf.

Flower: The plant blooms in great abundance all year in southern Florida, with lighter bloom in summer months.

*Form.*—Double — varies from $6\frac{1}{2}$ to 7 inches across the flower.

*Petals.*—Petals are 10 to 12 in number.

*Color.*—The base of the petal is 155-D White with $1\frac{1}{2}''$ Splash 55-C Neyron Rose HCC 623/2. All white — outside ring — $\frac{1}{2}''$ shades 8-C Mimosa Yellow HCC-602/2 to 8-A Mimosa Yellow HCC-602. Back of Petal: 155-D White to 8-C Mimosa Yellow Hcc-602/2 to 8-A Mimosa Yellow HCC-602.

*Veins.*—Slightly lighter than leaves.

*Stigma pads.*—Indian Yellow 17-A.

*Style.*—Style is 2 inches long, 155-D White.

I claim:

1. A new and distinct variety of hibiscus plant, of Rosa-sinensis species, substantially as herein described and illustrated, and characterized particularly as to novelty by its vigorous, upright habit of growth, its crisp green foliage, and its brilliant flowers.

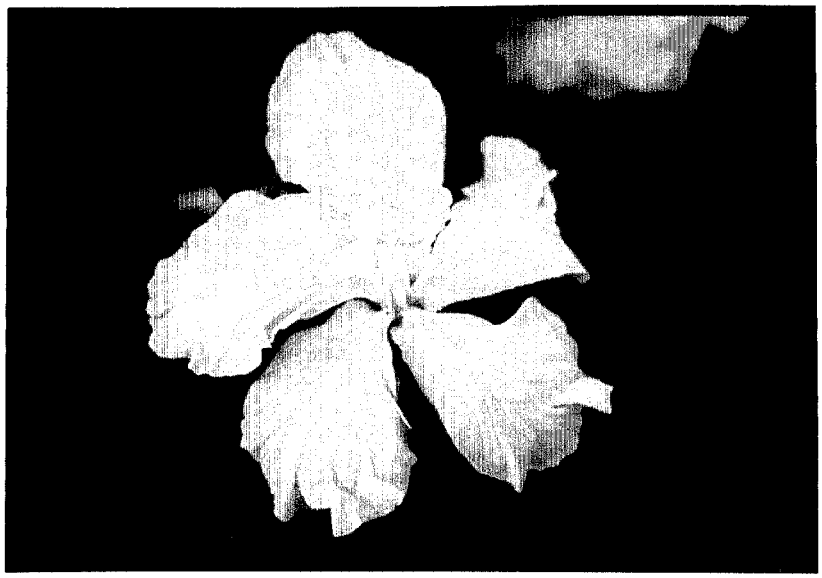
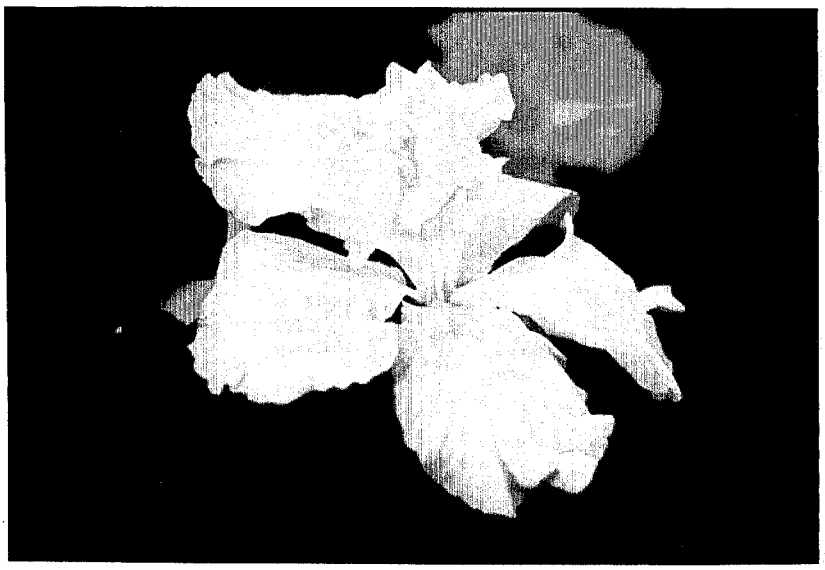

* * * * *